United States Patent [19]

Valyocsik et al.

[11] Patent Number: 4,973,781

[45] Date of Patent: Nov. 27, 1990

[54] ZEOLITE ZSM-57 AND CATALYSIS THEREWITH

[75] Inventors: Ernest W. Valyocsik; Nancy M. Page, both of Yardley, Pa.; Cynthia T-W. Chu, Princeton, N.J.

[73] Assignee: Mobil Oil Corporation, New York, N.Y.

[21] Appl. No.: 378,107

[22] Filed: Jul. 11, 1989

Related U.S. Application Data

[60] Division of Ser. No. 121,544, Nov. 17, 1982, Pat. No. 4,873,067, said Ser. No. 121,544, is a continuation-in-part of Ser. No. 944,297, Dec. 19, 1986, abandoned, and a continuation-in-part of Ser. No. 807,424, Dec. 10, 1985, abandoned, which is a continuation-in-part of Ser. No. 642,964, Aug. 21, 1984, abandoned, which is a continuation-in-part of Ser. No. 642,965, Aug. 21, 1984, abandoned, which is a continuation-in-part of Ser. No. 642,963, Aug. 21, 1984, abandoned, which is a continuation-in-part of Ser. No. 642,962, Aug. 21, 1984, abandoned, which is a continuation-in-part of Ser. No. 642,961, Aug. 21, 1984, abandoned, which is a continuation-in-part of Ser. No. 759,377, Jul. 26, 1985, abandoned, said Ser. No. 944,297, is a continuation-in-part of Ser. No. 759,377, Jul. 26, 1985, abandoned, which is a continuation-in-part of Ser. No. 642,964, Aug. 21, 1984, abandoned, which is a continuation-in-part of Ser. No. 642,965, Aug. 21, 1984, abandoned, which is a continuation-in-part of Ser. No. 642,963, Aug. 21, 1984, abandoned, which is a continuation-in-part of Ser. No. 642,962, Aug. 21, 1984, abandoned, which is a continuation-in-part of Ser. No. 642,961, Aug. 21, 1984, abandoned, which is a continuation-in-part of Ser. No. 642,930, Aug. 21, 1984, abandoned.

[51] Int. Cl.$^5$ .................... C07C 2/54; C07C 2/66; C07C 1/20; C07C 6/00

[52] U.S. Cl. .................... 585/467; 585/415; 585/417; 585/469; 585/475; 585/640

[58] Field of Search ............ 585/415, 417, 640, 469, 585/467, 475

[56] References Cited

U.S. PATENT DOCUMENTS

| | | | |
|---|---|---|---|
| 3,306,922 | 2/1967 | Barrer et al. | 260/443 |
| 3,966,883 | 6/1976 | Vaughn | 423/329 |
| 3,992,466 | 11/1976 | Plank et al. | 260/671 C |
| 4,000,248 | 12/1976 | Martin | 423/328 T |
| 4,016,245 | 4/1977 | Plank | 423/328 |
| 4,025,571 | 5/1977 | Lago | 423/328 T |
| 4,081,490 | 3/1978 | Plank et al. | 423/328 T |
| 4,124,686 | 11/1978 | Grose et al. | 423/328 T |
| 4,146,584 | 3/1979 | Rollman | 423/328 |
| 4,241,036 | 12/1980 | Flanigen et al. | 423/328 |
| 4,375,573 | 3/1983 | Young | 585/475 |
| 4,427,789 | 1/1984 | Miale et al. | 423/328 |
| 4,585,638 | 4/1986 | Kuhl | 423/328 |
| 4,585,639 | 4/1986 | Szostak | 423/328 |
| 4,623,530 | 11/1986 | Cullo et al. | 423/331 |
| 4,639,358 | 1/1987 | Derouane et al. | 423/329 |
| 4,640,829 | 2/1987 | Rubin | 423/328 |
| 4,709,114 | 11/1907 | Rodewald et al. | 585/640 |
| 4,717,780 | 1/1988 | Olson et al. | 585/467 |
| 4,729,979 | 3/1988 | Zletz | 502/202 |
| 4,873,067 | 10/1989 | Valyolsik et al. | 423/279 |

FOREIGN PATENT DOCUMENTS

| | | |
|---|---|---|
| 0049386 | 4/1982 | European Pat. Off. . |
| 174121 | 3/1986 | European Pat. Off. . |

OTHER PUBLICATIONS

*Zeolite Molecular Sieves,* Donald W. Breck, John Wiley and Sons, Inc., 1974 pp. 347-374.

"The Role of Organic Molecules in Molecular Sieve Synthesis", Lok et al, Zeolites, vol. 3, No. 4, Oct. 1983, pp. 282-291.

*Primary Examiner*—Asok Pal
*Attorney, Agent, or Firm*—Alexander J. McKillop; Charles J. Speciale; Edward F. Kenehan, Jr.

[57] ABSTRACT

This invention relates to a synthetic porous zeolite, identified as ZSM-57, a method for its preparation and use thereof in catalytic conversion of organic compounds. This crystalline material may have a ratio of $XO_2$: $Y_2O_3$ of at least 4, wherein X represents silicon and/or germanium and Y represents aluminum, boron, chromium, iron and/or gallium. The silica/alumina form of this crystalline material has a silica to alumina ratio of at least 4 and may be prepared with directing agents which are N,N,N,N',N',N'-hexaethylpentanediammonium compounds. The crystalline material exhibits a characteristic X-ray diffraction pattern.

12 Claims, No Drawings

ZEOLITE ZSM-57 AND CATALYSIS THEREWITH

CROSS-REFERENCE TO RELATED APPLICATIONS

This application is a division of copending U.S. Application Ser. No. 121,544, filed Nov. 17, 1982, now U.S. Pat. No. 4,873,067.

Said U.S. Application Ser. No. 121,544 is a continuation-in-part of U.S. Application Ser. No. 944,297, filed Dec. 19, 1986, now abandoned.

Said U.S. Application Ser. No. 121,544 is a continuation-in-part of U.S. Application Ser. No. 807,424, filed Dec. 10, 1985, now abandoned, which is a continuation-in-part of the following applications:

| SER. NO. | FILING DATE | STATUS |
|---|---|---|
| 642,964 | August 21, 1984 | Now abndoned |
| 642,965 | August 21, 1984 | Now abandoned |
| 642,963 | August 21, 1984 | Now abandoned |
| 642,962 | August 21, 1984 | Now abandoned |
| 642,961 | August 21, 1984 | Now abandoned |
| 759,377 | July 26, 1985 | Now abandoned |

Said U.S. Application Ser. No. 944,297 is also a continuation-in-part of said application Ser. No. 759,377 which is a continuation-in-part of the following applications:

| SER. NO. | FILING DATE | STATUS |
|---|---|---|
| 642,964 | August 21, 1984 | Now abandoned |
| 642,965 | August 21, 1984 | Now abandoned |
| 642,963 | August 21, 1984 | Now abandoned |
| 642,962 | August 21, 1984 | Now abandoned |
| 642,961 | August 21, 1984 | Now abandoned |
| 642,930 | August 21, 1984 | Now abandoned |

The entire disclosures of the above-identified applications are expressly incorporated herein by reference.

BACKGROUND

This invention relates to zeolite ZSM-57, to a method for its preparation and to its use in catalytic conversion of organic compounds.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. The zeolites have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U. S. Pat. No. 3,832,449), zeolite ZSM-20 (U.S. Pat. No. 3,972,983), ZSM-35 (U.S. Pat. No. 4,016,245), ZSM-38 (U.S. Pat. No. 4,046,859), and zeolite ZSM-23 (U.S. Pat. No. 4,076,842) to name a few.

The $SiO_2/Al_2O_3$ mole ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to infinity. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5 type zeolites. U.S. Pats. Nos. 4,061,724, 4,073,865 and 4,104,294 describe crystalline silicates or organosilicates of varying alumina and metal content.

A number of synthetic zeolites have been prepared which may be said to be isostructural with naturally occurring zeolites. Zeolites ZSM-35 and ZSM-38 are, for instance, ferrierite-type zeolites. Zeolite ZK-20 (U.S. Pat. No. 3,459,676) is described as being isostructural with the naturally occurring zeolite levynite.

Although zeolites include materials containing silica and alumina, it is recognized that the silica and alumina portions may be replaced in whole or in part with other oxides. More particularly, $GeO_2$ is an art recognized substitute for $SiO_2$ and $B_2O_3$, $Cr_2O_3$, $Fe_2O_3$, and $Ga_2O_3$ are art recognized replacements for $Al_2O_3$. Accordingly, the term zeolite as used herein shall connote not only materials containing silicon and, optionally, aluminum atoms in the crystalline lattice structure thereof, but also materials which contain suitable replacement atoms for such silicon and/or aluminum. On the other hand, the term aluminosilicate zeolite as used herein shall define zeolite materials consisting essentially of silicon and, optionally, aluminum atoms in the crystalline lattice structure thereof, as opposed to materials which contain substantial amounts of suitable replacement atoms for such silicon and/or aluminum.

The entire disclosures of the above-mentioned U.S. patents are also expressly incorporated herein by reference.

SUMMARY

The present invention is directed to zeolite ZSM-57, a method for its preparation and the conversion of organic compounds contacted therewith.

The zeolite of the present invention may have a ratio of $XO_2$: $Y_2O_3$ of at least 4, wherein X represents silicon and/or germanium and Y represents aluminum, boron, chromium, iron and/or gallium. Preferably, there are from greater than 8 to about 200 moles of $XO_2$ per mole of $Y_2O_3$. Preferably, $XO_2$ is silica and $Y_2O_3$ is alumina. It will be understood that each mole of Y will be associated with one mole of a cation.

The term directing agent, as used herein, shall connote organic or organometallic compounds which are added to the crystallization mixture used to form a zeolite in order to influence the morphology of the ultimately formed crystal lattice. At least a portion of the cations corresponding to the directing agent are bound to anionic sites of the crystal lattice in the as synthesized form of the zeolite. A directing agent which has been verified as capable of influencing the formation of the zeolite of the present invention, provided that other sufficient formation conditions are met, is an N,N,N,N',N',N'-hexaethylpentane- diammonium cation, hereinafter also referred to as Hexaethyl-DIQUAT-5. This cation may be supplied to the crystallization mixture, e.g., in the form of a bromide salt.

A means for identifying a zeolite of the present invention is by the X-ray diffraction pattern thereof. It will be understood that not all zeolites of the same structure will generate exactly the same X-ray diffraction data. For example, variations can occur which are attributable to the presence of impurities, e.g., in the form of occluded materials or crystalline intergrowths. The sodium forms in comparison with other cationic forms of otherwise identical zeolites reveal substantially the same patterns with some minor shifts in interplanar spacing and variation in relative intensity. Other minor variations can occur, depending on the silicon to aluminum ratio of the particular sample, as well as its degree of thermal treatment.

Zeolites in accordance with the present invention have X-ray diffraction lines as set forth in Table 1.

TABLE 1

| d ± delta d(Angstrom) | Intensity Range |
| --- | --- |
| 11.36 ± 0.23 | M-VS |
| 9.41 ± 0.19 | M-VS |
| 7.12 ± 0.15 | M-S (shoulder) |
| 6.95 ± 0.14 | M-S |
| 5.74 ± 0.12 | M |
| 5.68 ± 0.12 | W-M (shoulder) |
| 5.42 ± 0.11 | M-S |
| 4.81 ± 0.10 | W-M |
| 3.98 ± 0.08 | VW-M |
| 3.84 ± 0.08 | M-S (shoulder) |
| 3.79 ± 0.08 | VS |
| 3.64 ± 0.08 | W |
| 3.55 ± 0.08 | S |
| 3.48 ± 0.08 | S-VS |
| 3.36 ± 0.07 | W |
| 3.14 ± 0.07 | M-S |
| 3.06 ± 0.07 | W |
| 2.949 ± 0.06 | VW |
| 2.316 ± 0.05 | VW |
| 1.935 ± 0.04 | W |

Initial observations of ZSM-57 indicated that the x-ray diffraction pattern therefor lacked a line at 6.61±0.15 Angstroms (13.09–13.71 2X Theta). More particularly, when this region was scanned at a normal rate of 0.04 degree step intervals with counts taken for 4 seconds at each step, no line could be seen in this region (13.09–13.71 2X Theta). However, a more recent scan of this region at a much slower rate revealed a line of extremely weak intensity for a ZSM-57 sample. More particularly, when a ZSM-57 sample was scanned in this region at the extraordinary slow rate of 180 second counts per 0.01 step intervals, a very small line became resolved from the background having a relative intensity approximated to be less than one.

ZSM-57 is distinguished from ferrierite-type zeolites, such as ZSM-35, on the basis of the x-ray diffraction pattern for ZSM-57 as set forth in Table 1. It is further noted that x-ray diffraction patterns for ferrierite-type zeolites show a rather prominent line with a relative intensity greater than one at 6.61±0.15 Angstroms (13.09–13.71 2X Theta). Accordingly, species of ZSM-57 may be further distinguished from ferrierite-type zeolites, such as ZSM-35, by the absence of a readily observable line with a relative intensity of greater than one at 6.61±0.15 Angstrom (13.09–13.71 2X Theta).

The following Table 2 gives X-ray diffraction data for the uncalcined, as synthesized form of the zeolite prepared in accordance with Example 4, set forth hereafter.

TABLE 2

| Interplanar D-spacing (A) | Degrees 2 Theta | Relative Intensity, I/Io |
| --- | --- | --- |
| 11.37 | 7.77 | 19.3 |
| 9.41 | 9.39 | 29.6 |
| 7.11 | 12.44 | 16.2 |
| 6.97 | 12.69 | 25.2 |
| 5.74 | 15.43 | 28.4 |
| 5.69 | 15.56 | 16.5 |
| 5.42 | 16.32 | 38.2 |
| 4.70 | 18.84 | 9.5 |
| 3.83 | 23.22 | 39.5 |
| 3.78 | 23.49 | 100.0 |
| 3.74 | 23.75 | 12.9 |
| 3.64 | 24.45 | 13.1 |
| 3.56 | 25.00 | 48.1 |
| 3.48 | 25.60 | 56.2 |
| 3.36 | 26.53 | 7.9 |
| 3.13 | 28.46 | 34.2 |
| 3.04 | 29.36 | 10.1 |
| 2.95 | 30.30 | 5.1 |
| 2.81 | 31.77 | 1.0 |
| 2.66 | 33.61 | 2.8 |

The following Table 3 gives X-ray diffraction data for the calcined form of the zeolite prepared in accordance with Example 3, set forth hereinafter.

TABLE 3

| Interplanar D-spacing (A) | Degrees 2 Theta | Relative Intensity, I/Io |
| --- | --- | --- |
| 11.25 | 7.85 | 63.2 |
| 9.97 | 8.86 | 2.7 |
| 9.37 | 9.46 | 6.41 |
| 7.04 | 12.56 | 40.0 |
| 6.91 | 12.80 | 50.2 |
| 5.70 | 15.53 | 30.0 |
| 5.64 | 15.69 | 24.3 |
| 5.39 | 16.44 | 32.6 |
| 4.78 | 18.55 | 18.7 |
| 4.68 | 18.94 | 6.3 |
| 4.58 | 19.36 | 1.5 |
| 3.91 | 22.78 | 9.9 |
| 3.81 | 23.34 | 37.9 |
| 3.76 | 23.64 | 100.0 |
| 3.71 | 23.95 | 12.0 |
| 3.62 | 24.58 | 12.9 |
| 3.53 | 25.18 | 55.3 |
| 3.46 | 25.75 | 56.0 |

TABLE 3-continued

| Interplanar D-spacing (A) | Degrees 2 Theta | Relative Intensity, I/Io |
|---|---|---|
| 3.34 | 26.66 | 15.5 |
| 3.31 | 26.90 | 10.1 |
| 3.12 | 28.61 | 42.7 |
| 3.30 | 29.42 | 13.5 |
| 3.02 | 29.48 | 17.6 |
| 2.93 | 30.46 | 7.4 |
| 2.80 | 31.95 | 1.8 |
| 2.73 | 32.79 | 1.0 |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 $I/I_0$, where $I_0$ is the intensity of the strongest line or peak, and d (obs.) the interplanar spacing in Angstrom units (A), corresponding to the recorded lines, were determined. In Tables 2 and 3, the relative intensities are given in terms of the strongest line being taken as 100.0.

DESCRIPTION OF SPECIFIC EMBODIMENTS

The original alkali metal cations of the as synthesized zeolite can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which render the zeolite catalytically active, especially for hydrocarbon conversion. Replacing cations include hydrogen, rare earth metals and metals of Groups IA, IIA, IIIA, IVA, IB, IIB, IIIB, IVB and VIII of the Periodic Table of the Elements.

A typical ion exchange technique would be to contact the synthetic zeolite with a salt of the desired replacing cation or cations. Examples of such salts include the halides, e.g. chlorides, nitrates and sulfates.

The zeolite of the present invention sorbs significant amounts of commonly used test adsorbate materials, i.e. cyclohexane, n-hexane and water. Sorption capacities for the zeolite of the present invention may range at room temperature as follows:

| Adsorbate | Capacity, Wt. Percent |
|---|---|
| n-hexane | 6–7 |
| cyclohexane | 3–6 |
| water | 5–8 | wherein cyclohexane and n-hexane sorption are measured at 20 Torr and water sorption is measured at 12 Torr.

The zeolite of the present invention can be used either in the alkali metal form, e.g. the sodium or potassium form; the ammonium form; the hydrogen form or another univalent or multivalent cationic form. When used as a catalyst the zeolite will be subjected to thermal treatment to remove part or all of the organic constituent.

The zeolite can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be exchanged into the composition to the extent atom Y, e.g., aluminum, is in the structure, impregnated therein or intimately physically admixed therewith. Such component can be impregnated in or on to it such as for example, by, in the case of platinum, treating the zeolite with a solution containing a platinum metal-containing ion. Thus, suitable platinum compounds include chloroplatinic acid, platinous chloride and various compounds containing the platinum amine complex.

The zeolite of the present invention, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product is particularly useful in the catalysis of certain hydrocarbon conversion reactions.

The zeolite of the present invention, when employed either as an adsorbent or as a catalyst in an organic compound conversion process should be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing the zeolite in a vacuum, but a longer time is required to obtain a sufficient amount of dehydration.

The zeolite of the present invention can be prepared from a reaction mixture containing sources of alkali metal ions (Z), an oxide of Y, an oxide of X, a divalent N,N,N,N',N',N'-hexaethylpentane-diammonium cation (R), and water. The reaction mixture may comprise an appropriate selection of reactants, capable of forming the zeolite of the present invention, and having a composition falling within the following ranges:

| Reactants | Broad | Preferred |
|---|---|---|
| $SiO_2/Al_2O_3$ | 20–200 | 40–100 |
| $H_2O/SiO_2$ | 10–200 | 20–50 |
| $OH^-/SiO_2$ | 0–3 | 0.1–0.5 |
| $Z/SiO_2$ | 0–3 | 0.1–2 |
| $R/SiO_2$ | 0.01–2 | 0.1–1 | wherein R and Z are as above defined. The zeolites of the present invention may have a composition, expressed in terms of moles of oxides on an anhydrous basis, as follows:

$$(0-15)RO:(0-5)Z_2O:100SiO_2:(0.5-25)Al_2O_3$$

where R and Z are as defined above.

The divalent N,N,N,N',N',N'-hexaethylpentane-diammonium cation may be supplied by suitable compounds of the formula $$X(C_2H_5)_3N^+(CH_2)_5N^+(C_2H_5)_3X'$$

where X and X' are the same or different and are appropriate counterbalancing anions such as fluoride, chloride, bromide, iodide, hydroxide, acetate, sulfate, carboxylate, etc.

Crystallization of the zeolite of the present invention can be carried out at either static or stirred conditions in a suitable reactor vessel, such as for example, polypropylene jars or teflon lined or stainless steel autoclaves. A useful range of temperatures for crystallization is from about 80° C. to about 350° C. for a time of about 12 hours to about 200 days. Thereafter, the crystals are separated from the liquid and recovered. The composition can be prepared utilizing materials which supply the appropriate oxides. Such compositions may include sodium silicate, silica hydrosol, silica gel, silicic acid, sodium hydroxide, a source of aluminum, and an appropriate organic compound. It should be realized that the reaction mixture component oxides can be supplied from more than one source. The reaction mixture can be prepared either batchwise or continuously. Crystal size and crystallization time of the crystalline zeolite of the present invention will vary with the nature of the reaction mixture employed and the crystallization conditions.

In all cases, synthesis of the crystals of the zeolite of the present invention is facilitated by the presence of at least 0.01 wt. percent, preferably 0.10 wt. percent and still more preferably 1 wt. percent, seed crystals (based on total weight) of crystalline product.

It will be readily understood by those of ordinary skill in the art that the above recitation of useful and preferred ranges of reactants does not constitute a warranty that all possible combinations of reactants falling within these ranges will automatically lead to the production of a zeolite in accordance with the present invention. Accordingly, one must select reactants and crystallization conditions in a manner sufficient to lead to the formation of the zeolite of the present invention. This selection will be readily enabled by the guidance provided herein, especially with regard to the Examples recited hereinafter. In this regard, unsuccessful first attempts in the course of routine experimentation, which depart from the express reactant selections and conditions of the Examples recited hereinafter, could be followed by second attempts more closely corresponding with the express reactant selections and conditions of the Examples recited hereinafter.

It is further noted that the use of an appropriate seed crystal could theoretically change reactant mixture not capable of forming the zeolite of the present invention to a mixture capable of forming the zeolite of the present invention.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In the case of many catalysts, it is desired to incorporate the zeolite with another material resistant to the temperatures and other conditions employed in organic conversion processes. Such materials include active and inactive material and synthetic or naturally occurring zeolites as well as inorganic materials such as clays, silica and/or metal oxides, e.g. alumina. The latter may be either naturally occurring or in the form of gelatinous precipitates or gels including mixtures of silica and metal oxides. Use of a material in conjunction with the zeolite crystal, i.e. combined therewith, which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powderlike materials. These clay binders have been employed normally only for the purpose of improving the crush strength of the catalyst.

Naturally occurring clays which can be composited with the crystals of the present invention include the montmorillonite and kaolin families which include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the zeolite of the present invention can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The relative proportions of finely divided crystalline material and inorganic oxide gel matrix vary widely, with the zeolite content ranging from about 1 to about 90 percent by weight and more usually, particularly when the composite is prepared in the form of beads, in the range of about 2 to about 80 weight percent of the composite.

The zeolite of the present invention is useful as a catalyst component for a variety of organic, e.g. hydrocarbon, compound conversion processes. Such conversion processes include, as non-limiting examples, cracking hydrocarbons with reaction conditions including a temperature of from about 300° C. to about 700° C., a pressure of from about 0.1 atmosphere (bar) to about 30 atmospheres and a weight hourly space velocity of from about 0.1 to about 20; dehydrogenating hydrocarbon compounds with reaction conditions including a temperature of from about 300° Cc to about 700° C., a pressure of from about 0.1 atmosphere to about 10 atmospheres and a weight hourly space velocity of from about 0.1 to about 20; converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g. benzene, toluene and xylenes, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g. methanol, or ethers, e.g. dimethylether, or mixtures thereof to hydrocarbons including aromatics with reaction conditions including a temperature of from about 300° C. to about 550° C., more preferably from about 370° C. to about 500° C., a pressure of from about 0.01 psi to about 2000 psi, more preferably from about 0.1 psi to about 500 psi, and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure of from about atmospheric to about 60 atmospheres and a weight hourly space velocity of from about 0.08 to about 20; alkylating aromatic hydrocarbons, e.g. benzene and alkylbenzenes, in the presence of an alkylating agent, e.g. olefins, formaldehyde, alkyl halides and alcohols, with reaction conditions including a temperature of from about 340° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

Particular catalytic conversions for which the zeolite of the present invention can be used include (i) toluene disproportionation, (ii) toluene alkylation with methanol, (iii) propane (e.g., essentially pure propane) conversion to hydrocarbon mixtures enriched in BTX, (iv) upgrading refinery off-gas to liquid products enriched in BTX, and conversion of $C_1$-$C_4$ alcohols and/or $C_2$-$C_4$ ethers to hydrocarbons. It will be understood that BTX stands for aromatic hydrocarbon mixtures composed of two or more of benzene, toluene, xylene and ethylbenzene. The refinery off-gas is composed primarily of $C_1$-$C_3$ hydrocarbons and, optionally, hydrogen. This refinery off-gas will comprise at least 10% by weight of olefins (i.e. ethylene and/or propylene).

In order to more fully illustrate the nature of the invention and the manner of practicing same, the following examples are presented. In the examples, whenever adsorption data are set forth for comparison of sorptive capacities for water, cyclohexane and/or n-hexane, they were determined as follows:

A weighed sample of the calcined adsorbent was contacted with the desired pure adsorbate vapor in an adsorption chamber, evacuated to 1 mm and contacted with 12 mm Hg of water vapor or 20 mm Hg of n-hexane, or cyclohexane vapor, pressures less than the vapor-liquid equilibrium pressure of the respective adsorbate at room temperature. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined absorbent.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha Value of 1 (Rate Constant=0.016 sec$^{-1}$). The Alpha Test is described in U.S. Pat. No. 3,354,078 and in The Journal of Catalysis, Vol. IV, pp. 522–529 (August 1965). The Constraint Index is a measure of the selectivity of the particular catalyst and it involves conversion of normal hexane and 3-methylpentane. This test is described in many U.S. patents, including U.S. Pat. Nos. 4,231,899 and 4,288,647.

EXAMPLES 1–8

Synthesis reaction mixtures were prepared with compositions indicated in TABLE 4. The mixtures were prepared with Q-brand sodium silicate (PQ Corporation: 27.8% $SiO_2$, 8.4% $Na_2O$), $Al_2(SO_4)_3 \cdot 16H_2O$, Hexaethyl-Diquat-5 (bromide salt) and water. The mixtures were maintained at 160° C. for a number of days in a stainless steel, stirred (400 rpm) autoclave when crystallization was complete. The solids were separated from any unreacted components by filtration and then water washed, followed by drying at 110° C.

TABLE 4

Synthesis of Zeolite Samples
(160° C., stirred)
Mixture Composition (Mole Ratios)[a]

| Example No. | $SiO_2/Al_2O_3$ | $H_2O/SiO_2$ | $OH^-/SiO_2$ | $Na^+/SiO_2$ | $R^b/SiO_2$ | Time, Days |
|---|---|---|---|---|---|---|
| 1 | 90 | 40 | 0.40 | 0.59 | 0.10 | 5 |
| 2 | 90 | 40 | 0.30 | 0.59 | 0.10 | 6 |
| 3 | 60 | 40 | 0.30 | 0.59 | 0.10 | 7 |
| 4 | 60 | 40 | 0.30 | 0.59 | 0.08 | 5 |
| 5 | 60 | 40 | 0.20 | 0.59 | 0.10 | 6 |
| 6 | 60 | 40 | 0.30 | 0.59 | 0.10 | 4 |
| 7 | 50 | 40 | 0.30 | 0.59 | 0.10 | 4 |
| 8 | 40 | 40 | 0.30 | 0.59 | 0.15 | 5 |

[a]Q-brand sodium silicate; $Al_2(SO_4)_3 \cdot 16H_2O$.
[b]$R = (C_2H_5)_3N^+(CH_2)_5N^+(C_2H_5)_3$ = Hexaethyl-Diquat-5 (bromide salt).

The zeolite of the present invention was produced in accordance with each of Examples 1–8, except that Examples 1 and 2 also produced a detectable amount of alpha quartz, the amount of alpha quartz in the Example 1 zeolite being merely a trace.

The directing agent N,N,N,N',N',N'-hexaethylpentane-diammonium dibromide employed in crystallizing the zeolite of the present invention was prepared by refluxing overnight 1,5-dibromopentane with excess triethylamine in absolute ethanol. Analytical data for zeolite samples are compiled in Table 5. $SiO_2/Al_2O_3$ ratios for the zeolite range from 41–69. Aluminum present in the zeolite appears to be present as framework aluminum.

Also in Table 5, the compositions of the samples have been calculated on the basis of $100(SiO_2+AlO_2^-)$ tetrahedra. If it is assumed that the diquaternary cation employed to direct the crystallization is trapped intact within the structure during synthesis, then, from the analytical data, one can calculate an average of 2-3 Hexaethyl-Diquat-5 cations per 100 tetrahedra in the zeolite structure.

TABLE 5

Analytical Data for Zeolite Samples

| Sample | C/N | Moles per mole $Al_2O_3$ | | | Composition[a] | | | |
|---|---|---|---|---|---|---|---|---|
| | | $N_2O$ | $Na_2O$ | $SiO_2$ | Al 100 $T_d$ | $Na^+$ 100 $T_d$ | N 100 $T_d$ | $R^b$ 100 $T_d$ |
| 1 | 10.2 | 1.3 | 0.84 | 69 | 2.8 | 2.4 | 3.6 | 2.2 |
| 2 | 8.6 | 1.3 | 0.53 | 68 | 2.9 | 1.5 | 3.7 | 1.9 |
| 3 | 8.7 | 1.2 | 0.28 | 43 | 4.4 | 1.2 | 5.4 | 2.7 |
| 4 | 10.1 | 1.2 | 0.63 | 45 | 4.3 | 2.7 | 5.2 | 3.1 |
| 5 | 8.6 | 1.5 | 0.33 | 48 | 4.0 | 1.3 | 6.1 | 3.1 |
| 6 | 7.3 | 1.4 | 0.31 | 41 | 4.6 | 1.4 | 6.4 | 2.8 |
| 7 | 10.8 | 1.0 | 0.21 | 43 | 4.4 | 0.92 | 4.6 | 2.9 |
| 8 | 7.7 | 1.5 | 0.98 | 36 | 5.3 | 5.2 | 7.9 | 3.6 |

[a] Calculated on the basis of $100(SiO_2 + AlO_2^-)$tetrahedra.
[b] $R = (C_2H_5)_3N^+(CH_2)_5N^+(C_2H_5)_3$.

As indicated previously herein, Table 2 sets forth the X-ray powder diffraction pattern data for the uncalcined, as synthesized form of the zeolite prepared in accordance with Example 4. Table 3 sets forth the X-ray powder diffraction pattern data for the calcined zeolite prepared in accordance with Example 3. This Example 3 sample was calcined in air for six hours at 550° C. Clearly, the framework structure of this zeolite is stable to high temperature air calcination.

From SEM photomicrographs the zeolite crystals produced at these conditions appear to have a platelet morphology.

Characterization data for the Example 3 zeolite are set forth in Table 6. The H-form of the zeolite sorbed by weight 7.1 wt % n-hexane, 4.7 wt % cyclohexane, and 6.7 wt% water at 25° C. Catalytic data is also set forth in Table 6. More particularly, Table 6 shows that the Example 3 zeolite ($SiO_2/Al_2O_3=43$) in the H-form also showed molecular shape selectivity (Constraint Index=6.3 at 650° F.) and high cracking activity (alpha=225).

TABLE 6

Characterization Data for Example 3 Zeolite
Sample No. Example 3
Form: Hydrogen; $SiO_2/Al_2O_3 = 43$

| I. | Sorptions | Wt. %; 25° C.[a] |
|---|---|---|
| | N-hexane | 7.1 |
| | Cyclohexane | 4.7 |
| | Water | 6.7 | a. Hydrocarbons, 20 mm; water, 12 mm

TABLE 6-continued

Characterization Data for Example 3 Zeolite
Sample No. Example 3
Form: Hydrogen; $SiO_2/Al_2O_3 = 43$

| II. | Catalytic Data |
|---|---|
| | Alpha = 225 |
| | Constraint Index = 6.3[b] |
| | $E_a$ = 13.8 Kcal/mole |
| | b. 650° F. |

EXAMPLE 9

The zeolite preparation procedure of Examples 1-8 was repeated except that sodium aluminate was used in place of $Al_2(SO_4)_3 \cdot 16H_2O$ and silica sol (30% $SiO_2$) was used in place of Q-brand sodium silicate. As shown in the results set forth in Table 7, only about 10% by weight of the zeolite of the present invention was obtained after 3 days.

TABLE 7

Synthesis of Zeolite of the Present Invention
(160° C., stirred)

| Example No. | Mixture Composition (Mole Ratios)[a] | | | | | Time/Days | Product |
|---|---|---|---|---|---|---|---|
| | $SiO_2/Al_2O_3$ | $H_2O/SiO_2$ | $OH^-/SiO_2$ | $Na^+/SiO_2$ | $R^b/SiO_2$ | | |
| 9 | 60 | 40 | 0.30 | 0.33 | 0.10 | 3 | 10% Crystn. |

[a] Silica sol (30% $SiO_2$); $NaAlO_2$.
[b] $R = (C_2H_5)_3N^+(CH_2)_5N^+(C_2H_5)_3$ = Hexaethyl-Diquat-5 (bromide salt).

EXAMPLE 10

Samples of the zeolite of Example 6 were tested for catalytic activity. These crystals were pelletized, sized to 14/25 mesh and screened in a quartz microreactor for activity and selectivity in a variety of para selective alkylation reactions. From SEM pictures it is estimated that the crystal dimensions of this zeolite preparation have a shortest crystal dimension of about 0.1 microns. Therefore, for comparison, a ZSM-5 crystal which has a $SiO_2/Al_2O_3=40$ and a shortest crystal dimension of 0.1 microns was also evaluated. Comparison of these two catalysts for selective toluene disproportionation, toluene alkylation with ethylene and toluene alkylation with methanol are presented in Tables 8-10, respectively.

TABLE 8

| | Toluene Disproportionation[1] | | | | | | | |
|---|---|---|---|---|---|---|---|---|
| Catalyst | Example 6 Zeolite | | | | HZSM-5 | | | |
| Temp. °C. | 450 | 500 | 550 | 600 | 450 | 500 | 550 | 600 |
| Toluene Conv., wt % | 45.0 | 43.1 | | 33.4 | 19.1 | 34.8 | 44.3 | 46.7 |
| Product Selectivity | | | | | | | | |
| Benzene | 42.3 | 46.7 | | 47.6 | 43.7 | 47.4 | 44.3 | 58.4 |

TABLE 8-continued

| Catalyst | Toluene Disproportionation[1] | | | | | | |
|---|---|---|---|---|---|---|---|
| | Example 6 Zeolite | | | | HZSM-5 | | |
| Ethylbenzene | 0.3 | 0.3 | 0.1 | 0.2 | 0.3 | 0.5 | 0.2 |
| Xylene | 48.3 | 48.0 | 48.2 | 54.2 | 49.4 | 41.5 | 37.7 |
| C$_9$+ | 9.0 | 4.8 | 4.2 | 1.8 | 2.7 | 3.6 | 3.7 |
| Xylene Isomer Distribution | | | | | | | |
| para | 24.0 | 23.9 | 23.4 | 24.1 | 23.6 | 23.5 | 23.3 |
| meta | 52.5 | 52.0 | 51.8 | 52.7 | 52.9 | 52.3 | 51.7 |
| ortho | 23.6 | 24.1 | 24.8 | 23.2 | 23.5 | 24.2 | 24.9 |

[1]Toluene WHSV = 5.5 hr$^{-1}$

TABLE 9

| Catalyst | Toluene Alkylation with Ethylene[1] | | | |
|---|---|---|---|---|
| | Example 6 Zeolite | | ZSM-5 | |
| Temp. °C. | 400 | 450 | 400 | 450 |
| Toluene Conv., wt % | 23.0 | 17.1 | 17.3 | 19.1 |
| Product Selectivity | | | | |
| Benzene | 20.9 | 18.9 | 20.0 | 32.9 |
| Ethylbenzene/Xylenes | 33.2 | 28.6 | 26.5 | 36.5 |
| Ethyltoluene | 36.0 | 42.6 | 40.9 | 19.4 |
| C$_9$+ | 7.0 | 8.0 | 7.2 | 7.7 |
| Ethyltoluene Isomer Distribution | | | | |
| para | 30.1 | 30.3 | 28.1 | 29.0 |
| meta | 53.4 | 52.9 | 56.9 | 51.8 |
| ortho | 16.5 | 16.8 | 15.1 | 19.1 |

[1]Toluene WHSV = 8.8 hr$^{-1}$, C$_2$H$_4$ WHSV = 0.5 hr. Toluene/C$_2$H$_4$ molar ratio = 5/1

TABLE 10

| Catalyst | Toluene Alkylation with Methanol[1] | | | | | |
|---|---|---|---|---|---|---|
| | Example 6 Zeolite | | | HZSM-5 | | |
| Temp. °C. | 400 | 500 | 600 | 400 | 500 | 600 |
| Toluene Conv., wt % | 31.9 | 35.3 | 30.2 | 21.7 | 34.2 | 38.5 |
| Product Selectivity | | | | | | |
| Benzene | 19.7 | 19.4 | 19.3 | 13.8 | 24.5 | 36.8 |
| Ethylbenzene | 0.4 | 0.1 | 0.1 | 0.9 | 0.5 | 0.3 |
| Xylene | 68.1 | 70.9 | 72.4 | 65.1 | 65.3 | 56.3 |
| C$_9$+ | 11.3 | 9.5 | 8.3 | 17.9 | 9.0 | 6.3 |
| Xylene Isomer Distribution | | | | | | |
| para | 23.5 | 23.4 | 23.4 | 24.1 | 23.8 | 23.7 |
| meta | 54.0 | 53.0 | 52.0 | 53.0 | 52.3 | 52.1 |
| ortho | 22.6 | 23.6 | 24.6 | 22.8 | 23.8 | 24.2 |

[1]Toluene/MeOH molar ratio = 4/1. Toluene WHSV = 15.8 hr$^{-1}$

For a Constraint Index of 6.3 for the Example 6 zeolite, it would be expected that this zeolite should exhibit shape-selective properties, but it should be slightly less shape selective with respect to large molecules than ZSM-5 which has a Constraint Index of 8.3. To measure the shape-selective characteristics of the example 6 zeolite relative to ZSM-5, a solution of phenyldodecanes in benzene was prepared. This solution was then passed over the two catalysts, the Example 6 zeolite and ZSM-5. Isomer distributions of the starting material and of the phenyldodecanes after reaction over the 0.1 micron ZSM-5 crystal and the Example 6 crystal are summarized in Table 11. As these results show, both ZSM-5 and the Example 6 zeolite are preferentially cracking the smaller 2-phenyldodecane isomer. However, ZSM-5 appears to be more shape-selective than the Example 6 zeolite in this reaction as it completely removes all the 2-isomer. While the Example 6 zeolite does significantly reduce the amount of 2-isomer present relative to the other isomers, it does not completely remove all of it.

TABLE 11

| | Phenyldodecane Cracking | | | |
|---|---|---|---|---|
| Catalyst | FEED | Example 6 Zeolite | | ZSM-5 | |
| Temp., °C. | | 150 | 200 | 150 | 200 |
| Isomer Distribution | | | | | |
| 6− | 15.9 | 27.4 | 27.1 | 26.3 | 26.5 |
| 5− | 14.6 | 26.4 | 26.1 | 26.5 | 27.4 |
| 4− | 14.6 | 23.1 | 22.9 | 25.3 | 24.8 |
| 3− | 16.5 | 18.2 | 17.1 | 22.0 | 21.3 |
| 2− | 37.4 | 4.8 | 6.7 | 0 | 0 |

As an additional comparison of the catalytic performance of the Example 6 zeolite and ZSM-5, the reaction of propane over these two catalysts was studied. Results are summarized in Table 12. These results show that ZSM-57 has appreciable aromatization activity, but it does not appear to be as effective as ZSM-5 in aromatization reactions.

TABLE 12

| | Propane Cracking[1] over Example 6 Zeolite and ZSM-5 | | | |
|---|---|---|---|---|
| Catalyst | Example 6 Zeolite | | ZSM-5 | |
| Temp., °C. | 500 | 600 | 500 | 600 |
| Propane Conv. | 28.0 | 46.4 | 35.0 | 94.7 |
| Product Selectivity | | | | |
| H$_2$ | 1.6 | 3.1 | 1.7 | 3.6 |
| C$_1$ | 23.9 | 23.9 | 26.3 | 44.0 |
| C$_2$ | 16.9 | 5.2 | 21.8 | 14.4 |
| C$_2$= | 6.6 | 22.5 | 3.3 | 4.6 |
| C$_3$= | 8.2 | 16.0 | 3.5 | 1.6 |
| C$_4$° | 1.6 | 1.9 | 4.4 | 0 |
| C$_4$= | 11.5 | 0.7 | 11.0 | 0.2 |
| C$_5$ | 1.5 | 0.9 | 0.8 | 0 |
| C$_6$ | 0.7 | 0.7 | 0.3 | 0.2 |
| BZ | 3.0 | 6.5 | 5.6 | 17.8 |
| Tol | 5.6 | 6.5 | 10.4 | 9.4 |
| C$_8$A | 5.1 | 4.5 | 8.4 | 2.6 |
| C$_9$A | 2.7 | 2.0 | 1.7 | 0.4 |
| C$_{10}$+ | 11.2 | 5.7 | 0.9 | 1.2 |
| BTX Selectivity | 13.7 | 17.5 | 24.4 | 29.8 |
| C$_2$=−C$_4$= Selectivity | 26.3 | 39.2 | 17.8 | 6.3 |

[1]Propane WHSV = 1.3 hr$^{-1}$

Subsequent to the generation of the data reported hereinabove, a sample of ZSM-35, which is known to have a ferrierite-type structure, was obtained for comparison of the catalytic performance of this ZSM-35 zeolite with that of the zeolite of the present invention. Results of these catalytic studies are summarized in Tables 13–15. For comparison purposes, catalytic data for the Example 6 zeolite and ZSM-5 under the same conditions are also reported.

TABLE 13

| | Propane Cracking | | |
|---|---|---|---|
| Catalyst | HZSM-35 | Example 6 Zeolite | HZSM-5 |
| Temp., °C. | 600 | 600 | 600 |

TABLE 13-continued

Propane Cracking

| Catalyst | HZSM-35 | Example 6 Zeolite | HZSM-5 |
|---|---|---|---|
| $C_3H_8$ WHSV | 1.3 | 1.3 | 1.3 |
| $C_3H_8$ Conv. | 58.3 | 69.3 | 99.3 |
| Product Distribution | | | |
| $H_2$ | 3.3 | 3.4 | 3.0 |
| $C_1$ | 38.8 | 28.1 | 41.8 |
| $C_2$ | 7.8 | 8.4 | 14.4 |
| $C_2=$ | 28.7 | 12.9 | 3.6 |
| $C_3=$ | 16.4 | 9.2 | 0.5 |
| $C_4$ | 0 | 11.7 | 0.05 |
| $C_4=$ | 3.1 | 0.6 | 0.02 |
| $C_5+$ Alip. | 0.4 | 0.6 | 0.05 |
| Aroms. | 1.2 | 25.2 | 36.7 |

TABLE 14

Toluene Disproportionation

| Catalyst | ZSM-35 | | Example 6 Zeolite | | ZSM-5 | |
|---|---|---|---|---|---|---|
| Temp., °C. | 500 | 600 | 500 | 600 | 500 | 600 |
| Toluene Conv., wt % | 2.7 | 2.7 | 43.1 | 33.4 | 34.8 | 46.7 |
| Product Selectivity | | | | | | |
| BZ | 53.5 | 66.7 | 46.7 | 47.6 | 47.4 | 58.4 |
| EB | 0.7 | 2.1 | 0.3 | 0.1 | 0.3 | 0.2 |
| Xyl | 45.8 | 29.7 | 48.0 | 48.2 | 49.4 | 37.7 |
| $C_9+$ | 0 | 1.7 | 4.8 | 4.2 | 2.7 | 3.7 |
| Isomer Distribution | | | | | | |
| para | 39.1 | 44.4 | 23.9 | 23.4 | 23.6 | 23.3 |
| meta | 43.7 | 39.9 | 52.0 | 51.8 | 52.9 | 51.7 |
| ortho | 17.3 | 19.7 | 24.1 | 24.8 | 23.5 | 24.9 |

Toluene WHSV = 5.5 hr$^{-1}$

TABLE 15

Toluene Alkylation with Ethylene

| Catalyst | ZSM-35 | | Example 6 Zeolite | | ZSM-5 | |
|---|---|---|---|---|---|---|
| Temp., °C. | 400 | 450 | 400 | 450 | 400 | 450 |
| Toluene Conv., wt % | 1.2 | 1.1 | 23.0 | 17.1 | 17.3 | 19.1 |
| Product Selectivity, wt % | | | | | | |
| BZ | 22.1 | 20.9 | 20.9 | 18.9 | 20.0 | 32.9 |
| EB/Xyl | 33.0 | 32.3 | 33.2 | 28.6 | 26.5 | 36.5 |
| ET | 44.9 | 46.8 | 36.0 | 42.6 | 40.9 | 19.4 |
| $C_9+$ | 0 | 0 | 7.0 | 8.0 | 7.2 | 7.7 |
| Isomer Distribution | | | | | | |
| para | 51.7 | 42.4 | 30.1 | 30.3 | 28.1 | 29.0 |
| meta | 37.8 | 44.1 | 53.4 | 52.9 | 56.9 | 51.8 |
| ortho | 10.6 | 13.5 | 16.5 | 16.8 | 15.1 | 19.1 |

Toluene WHSV = 8.8 hr$^{-1}$; $C_2H_4$ = 0.5 hr$^{-1}$.

Toluene/$C_2H_4$ molar ratio = 5/1

Toluene Disproportionation 2.0 gm of the Example 6 catalyst (sized to 14/25 mesh) is centered in a quartz microreactor. Low surface area quartz chips are used to position the catalyst and fill void spaces. After calcination with air at 500° C. for one hour, the reactor is flushed with nitrogen for approximately five minutes. The temperature is maintained at 500° C. and toluene is passed over the catalyst at the rate of 5.1 ml/hr (Toluene WHSV=2.2 hr$^{-1}$). A liquid sample is collected for the last 5 min. of a 30 min. run. The composition of the liquid is determined by gas chromatography using a SCOT Bentone column. The temperature is then increased rapidly and successively to 550° and 600° C. In a similar manner, liquid samples are taken for analysis during the last 5 min. of a 30 min. run. Results of tests conducted essentially in accordance with this procedure are provided in Table 16.

TABLE 16

Toluene Disproportionation Over the Example 6 Zeolite

| Temperature, °C. | 500° | 550° | 600° |
|---|---|---|---|
| Toluene Conversion, wt % | 53.2 | 54.2 | 53.9 |
| Product Selectivities, wt % | | | |
| Benzene | 49.1 | 51.3 | 53.2 |
| Ethylbenzene/Xylenes | 43.1 | 40.8 | 37.5 |
| $C_9+$ aromatics | 7.7 | 7.9 | 9.3 |
| Isomer Distribution, wt % | | | |
| p-xylene | 23.9 | 23.6 | 23.6 |
| m-xylene | 53.1 | 52.7 | 51.9 |
| o-xylene | 23.0 | 23.7 | 24.4 |

Toluene WHSV = 2.2 hr$^{-1}$

Toluene Alkylation with Methanol

The Example 6 zeolite is pelletized and sized to 14/25 mesh. 2.0 gm of this catalyst is placed in a quartz micro reactor with low surface area quartz chips used to center the catalyst and fill void spaces. The catalyst is calcined in air at 500° C. for one hour. The temperature is then adjusted to 400° C. and a mixture of toluene and methanol (4:1 molar ratio toluene:methanol) is passed over the catalyst. After 25 min. on stream, a liquid sample is collected for 5 min. for analysis. The temperature is then successively increased to 500° and 600° C. and the same procedure is repeated. The results of tests conducted essentially in accordance with this procedure are summarized in Table 17.

TABLE 17

Toluene Alkylation With Methanol over Example 6 Zeolite

| Temperature, °C. | 500° | 500° | 600° |
|---|---|---|---|
| Toluene WHSV, hr$^{-1}$ | 15.8 | 15.8 | 15.8 |
| Toluene Conversion, wt % | 31.9 | 35.3 | 30.2 |
| Product Selectivities, wt % | | | |
| Benzene | 19.7 | 19.4 | 19.3 |
| Xylenes | 68.2 | 70.9 | 72.4 |
| $C_9+$ Aromatics | 11.3 | 9.5 | 8.3 |
| Isomer Distribution, wt % | | | |
| p-xylene | 23.5 | 23.4 | 23.4 |
| m-xylene | 54.0 | 53.0 | 52.0 |
| o-xylene | 22.6 | 23.6 | 24.6 |

Propane Conversion

The Example 6 zeolite was pelletized and sized to 14/25 mesh. 2.0 gms of this catalyst was placed in a quartz reactor with low surface area quartz chips used to center the catalyst and fill void spaces. The catalyst is calcined in air at 500° C. Propane is then passed over the catalyst. Samples of reactor effluent are taken after 30 min. on stream and after 2.0 hrs. on stream. The same procedure is repeated at 550° C. and 600° C. with calcination between each temperature change. Results of tests conducted essentially in accordance with this procedure are shown in Table 18.

TABLE 18

Propane Conversion Over Example 6 Zeolite

| Temp., °C. | 500° | 500° | 550° | 550° | 600° | 600° |
|---|---|---|---|---|---|---|
| $C_3H_8$ WHSV, $hr^{-1}$ | 1.3 | 1.3 | 2.2 | 2.2 | 1.3 | 1.3 |
| Time on stream, hrs | 0.5 | 2.0 | 0.5 | 2.0 | 0.5 | 2.0 |
| Product Selectivity, wt % | | | | | | |
| $H_2$ | 1.7 | 1.6 | 1.9 | 2.0 | 3.9 | 3.1 |
| $CH_4$ | 26.8 | 23.9 | 33.7 | 30.1 | 32.3 | 23.8 |
| $C_2H_6$ | 21.5 | 16.9 | 19.0 | 14.1 | 9.6 | 5.2 |
| $C_2H_4$ | 4.6 | 6.6 | 7.6 | 11.2 | 14.8 | 22.5 |
| $C_3H_6$ | 4.5 | 8.2 | 7.8 | 12.7 | 10.6 | 16.0 |
| $C_4H_{10}$ | 1.1 | 1.6 | 1.9 | 2.7 | 1.2 | 1.9 |
| $C_4H_8$ | 10.6 | 11.5 | 6.5 | 5.8 | 0.7 | 0.7 |
| $C_5$ | 1.1 | 1.5 | 0.9 | 1.2 | 0.2 | 0.9 |
| $C_6$ | 0.4 | 0.8 | 0.9 | 1.2 | 0.4 | 0.7 |
| BZ | 4.0 | 3.0 | 4.5 | 3.8 | 7.8 | 6.5 |
| Tol | 7.6 | 5.6 | 7.3 | 6.8 | 9.0 | 6.5 |
| $C_8A$ | 7.4 | 5.1 | 5.5 | 5.8 | 5.3 | 4.6 |
| $C_9A$ | 2.6 | 2.7 | 1.7 | 1.9 | 1.6 | 2.0 |
| $C_{10}+$ | 6.2 | 11.2 | 0.8 | 0.9 | 2.7 | 5.7 |
| $C_3H_8$ Conversion | 36.5 | 28.0 | 44.0 | 32.3 | 67.0 | 46.4 |
| BTX Selectivity | 18.9 | 13.7 | 17.3 | 16.3 | 22.1 | 17.6 |
| $C_2^=-C_4^=$ Selec. | 19.6 | 26.3 | 22.0 | 29.6 | 26.0 | 39.1 |

Upgrading of Refinery Off Gas to Liquid Product Rich in BTX

The Example 6 zeolite was pelletized and sized to 14/25 mesh. 2.0 gms of this catalyst was placed in a quartz reactor with low surface area quartz chips used to center the catalyst and fill void spaces. The catalyst is calcined in air at 500° C. for one hour. A synthetic refinery off gas is then passed over the catalyst Reactor effluent is sampled at 0.5 hr. and 2.0 hrs. on stream. The catalyst is then calcined and the same procedure repeated at 600° C. Tests were conducted substantially in accordance with this procedure. Product distribution as well as the composition of the simulated refinery off gas are summarized in Table 19.

TABLE 19

Refinery Off Gas Upgrading Over Example 6 Zeolite

| Temp., °C. | | 500° | 500° | 600° | 600° |
|---|---|---|---|---|---|
| WHSV, $hr^{-1}$ | | 1.0 | 1.0 | 1.0 | 1.0 |
| Time on stream, hrs | | 0.5 | 2.0 | 0.5 | 2.0 |
| Composition, wt % | Feed | | | | |
| $H_2$ | 1.6 | 2.2 | 2.2 | 2.8 | 2.8 |
| $CH_4$ | 38.0 | 42.5 | 41.6 | 45.2 | 42.5 |
| $C_2H_6$ | 22.0 | 24.2 | 23.6 | 24.0 | 23.0 |
| $C_2H_4$ | 15.3 | 1.2 | 1.6 | 4.4 | 7.0 |
| $C_3H_8$ | 6.6 | 14.7 | 12.7 | 3.2 | 5.8 |
| $C_3H_6$ | 16.6 | 1.0 | 2.1 | 1.7 | 4.5 |
| $C_4H_{10}$ | | 0.4 | 0.6 | 0.3 | 0.7 |
| $C_4H_8$ | | 2.6 | 2.9 | 0.2 | 0.3 |
| $C_5$ | | 0.4 | 0.7 | 0.1 | 0.1 |
| $C_6$ | | 0.2 | 0.4 | 0.04 | 0.3 |
| BZ | | 2.2 | 1.8 | 5.3 | 3.9 |
| Tol | | 4.0 | 3.9 | 5.0 | 4.2 |
| $C_8A$ | | 3.2 | 3.8 | 2.6 | 2.5 |
| $C_9A$ | | 0.8 | 1.2 | 0.7 | 0.8 |
| $C_{10}+$ | | 0.3 | 1.0 | 4.6 | 1.6 |
| gms BTX/100 gms feed | | 9.2 | 9.4 | 14.2 | 11.7 |

Methanol Conversion

The ZSM-57 of Example 6 was used to convert methanol to hydrocarbons. The ZSM-57 was converted to H form prior to catalytic testing. Data are presented in Table 20. Runs 1 and 2 show the results of MeOH conversion at 370° C., atm pressure. The selectivity of the light olefins is about 67 wt % with ethylene selectivity greater than 30 wt %. Run 3 shows the result of MeOH conversion at 500° C., atm pressure. The selectivity of the light olefins is 21 wt % with 22 wt % of aromatics.

TABLE 20

| Run No. | 1 | 2 | 3 |
|---|---|---|---|
| Temp. (C.) | 370 | 370 | 500 |
| Pressure | atm | atm | atm |
| LHSV | 1 | 1 | 1 |
| TOS(hr) | 2.7 | 5.2 | 5.9 |
| % Conversion | 9.26 | 9.17 | 79.56 |
| Hydrocarbon selectivity (wt %) | | | |
| Methane | 5.69 | 5.05 | 11.71 |
| Ethane | 3.28 | 2.39 | 16.52 |
| Ethylene | 31.95 | 33.94 | 3.59 |
| Propane | 11.00 | 11.01 | 2.90 |
| Propene | 17.18 | 18.81 | 8.14 |
| i-Butane | 7.72 | 7.61 | 6.72 |
| n-butane | 2.32 | 1.74 | 1.31 |
| $C_4$ Olefins | 16.99 | 14.59 | 7.34 |
| i-Pentane | 1.93 | 2.84 | 1.94 |
| n-Pentane | 0.39 | 0.64 | 0.54 |
| $C_5$ Olefins | 1.06 | 0.92 | 1.89 |
| $C_6+$ PON | 0.48 | 0.46 | 14.99 |
| Benzene | — | — | 0.64 |
| Toluene | — | — | 0.29 |
| $C_8$ Aromatics | — | — | 4.44 |
| $C_9$ Aromatics | — | — | 9.25 |
| $C_{10}+$ Aromatics | — | — | 7.75 |
| $C_1-C_5$ Paraffins | 32.34 | 31.28 | 41.64 |
| $C_2-C_5$ Olefins | 67.18 | 68.26 | 20.96 |
| $C_6+$ PON | 0.48 | 0.46 | 14.99 |
| Aromatics | — | — | 22.38 |

It will be noted that the light olefins produced in accordance to this process could be converted to low-durene gasoline under known conditions with a zeolite catalyst such as ZSM-5.

In order to more fully demonstrate the present invention, the following examples are presented:

EXAMPLE 11

A first solution was made by dissolving 2.57 g $Al_2(SO_4)_3 \cdot 18$ $H_2O$ and 0.74 g $Na_2B_4O_7 \cdot 10$ $H_2O$ (sodium borate, decahydrate) in 83.7 g deionized water and then adding 1.99 g concentrated $H_2SO_4$ to the solution. Then 10.0 g Hexaethyl-DIQUAT-5 bromide [$BrEt_3N(CH_2)_5NEt_3Br=R$]quaternary ammonium salt was dissolved in the solution. A second solution was made by dissolving 50.0 g sodium silicate (27.8% $SiO_2$; 8.4% $Na_2O$; 63.8% $H_2O$) in 50.0 g deionized water.

The first solution was transferred to a 300 ml stainless-steel autoclave. The second solution was then added to the autoclave with stirring. The reaction mixture was stirred for two minutes at room temperature. The autoclave was sealed with stirring continued and heating started.

The hydrogel formed was described by the following mole ratios:

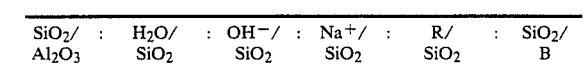

| -continued | | | | | | | | | | |
|---|---|---|---|---|---|---|---|---|---|---|
| 60 | : | 40 | : | 0.30 | : | 0.59 | : | 0.10 | : | 30 |

The hydrogel was reacted at 160° C., with stirring (400 rpm), for 4 days before quenching. The resultant product was filtered, washed, and dried under an infrared heat lamp before X-ray diffraction analysis. The X-ray analysis results proved the as-synthesized solid product to be boron-containing ZSM-57, contaminated with mordenite and alpha-quartz.

EXAMPLE 12

A first solution is made by dissolving 2.57 g $Al_2(SO_4)_3 \cdot 18\ H_2O$ and 0.55 g $Ga_2(SO_4)_3$ in 83.7 g deionized water and then adding 1.26 g concentrated $H_2SO_4$ to the solution. Then 10.0 g Hexaethyl-DIQUAT -5 bromide quaternary ammonium salt (R) is added to the solution. A second solution is made by dissolving 50.0 g sodium silicate (27.8% $SiO_2$; 8.4% $Na_2O$; 63.8% $H_2O$) in 50.0 g deionized water.

The first solution is added to a 300 ml stainless-steel autoclave to which the second solution is then added with stirring. The reaction mixture is stirred for two minutes at room temperature to achieve a uniform consistency, then the autoclave is sealed with stirring continued and heating started.

The resulting hydrogel is described by the mole ratios:

| $SiO_2/$ $Al_2O_3$ | : | $H_2O/$ $SiO_2$ | : | $OH^-/$ $SiO_2$ | : | $Na^+/$ $SiO_2$ | : | $R/$ $SiO_2$ | : | $SiO_2/$ Ga |
|---|---|---|---|---|---|---|---|---|---|---|
| 60 | : | 40 | : | 0.30 | : | 0.59 | : | 0.10 | : | 90 |

This hydrogel is reacted at 160° C., with stirring at 400 rpm, for 4 days before termination. The solid product is processed in the usual manner by filtering, washing and drying before X-ray diffraction analysis showing it to be gallinum-containing ZSM-57.

EXAMPLE 13

A first solution is made by dissolving 2.57 g $Al_2(SO_4)_3 \cdot 18\ H_2O$ and 1.04 g $Fe(NO_3)_3 \cdot 9\ H_2O$ in 83.3 g deionized water and then adding 0.74 g concentrated $H_2SO_4$ to the solution. Then 10.0 g Hexaethyl-DIQUAT -5 bromide quaternary ammonium salt (R) is dissolved in the solution. A second solution is made by dissolving 50.0 g sodium silicate (27.8% $SiO_2$; 8.4% $Na_2O$; 63.8% $H_2O$) in 50.0 g deionized water.

The first solution is placed in a 300 ml stainless-steel autoclave, to which the second solution is then added with stirring. The mixture is stirred for two minutes at room temperature before sealing the autoclave. The autoclave stirring and heating is begun immediately.

The hydrogel formed by the reaction mixtures is described by the mole ratios:

| $SiO_2/$ $Al_2O_3$ | : | $H_2O/$ $SiO_2$ | : | $OH^-/$ $SiO_2$ | : | $Na^+/$ $SiO_2$ | : | $R/$ $SiO_2$ | : | $SiO_2/$ Fe |
|---|---|---|---|---|---|---|---|---|---|---|
| 60 | : | 40 | : | 0.30 | : | 0.59 | : | 0.10 | : | 90 |

The crystallization is conducted at 160° C., with stirring at 400 rpm, for four days before termination. The solid product is processed by filtration, washing and drying before X-ray diffraction analysis showing it to be iron-containing ZSM-57.

EXAMPLE 14

A first solution is made by dissolving 2.57 g $Al_2(SO_4)_3 \cdot 18\ H_2O$ and 0.68 g $CrCl_3 \cdot 6\ H_2O$ in 83.3 g deionized water and then adding 1.00 g concentrated $H_2SO_4$ to the solution. The directing agent Hexaethyl-DIQUAT -5 bromide quaternary ammonium salt (R) is then added to the solution. A second solution is made by dissolving 50.0 g sodium silicate (27.8% $SiO_2$; 8.4% $Na_2O$; 63.8% $H_2O$) in 50.0 g deionized water.

The first solution is transferred to a 300 ml autoclave, then the second solution is stirred in. Stirring of the reaction mixture is continued for two minutes at room temperature before sealing the autoclave. Stirring and heating of the autoclave is begun immediately.

The hydrogel formed by the reaction mixtures is described by the mole ratios:

| $SiO_2/$ $Al_2O_3$ | : | $H_2O/$ $SiO_2$ | : | $OH^-/$ $SiO_2$ | : | $Na^+/$ $SiO_2$ | : | $R/$ $SiO_2$ | : | $SiO_2/$ Cr |
|---|---|---|---|---|---|---|---|---|---|---|
| 60 | : | 40 | : | 0.30 | : | 0.59 | : | 0.10 | : | 90 |

The crystallization is carried out for four days at 160° C., with stirring at 400 rpm, before termination. The solid product is processed as in Example 13 before X-ray diffraction analysis showing it to be chromium-containing ZSM-57.

EXAMPLE 15

Zeolite ZSM-57 made as in Example 6 is converted to the $NH^+_4$ form by first calcining the as-synthesized zeolite for 10 hours in air at 500° C., then $NH^+_4$-exchanging the air-calcined ZSM-57 for 4 hours in a 1M $NH_4NO_3$ solution at 80° C. After $NH^+_4$-exchange, the zeolite is filtered, washed and dried.

A 10.0 g sample of $NH_4$-ZSM-57 is placed into a one-liter polypropylene bottle to which is then added 500 ml of 0.2M $NH_4BF_4$, adjusted to ph 7 with ammonium acetate. The mixture is heated for 20 hours at 85° C. with stirring. After reaction, the product is filtered, washed with distilled water, dried under an infrared heat lamp, and found to be boron-containing ZSM-57.

EXAMPLE 16

A 0.2M $GaF_3$ solution is prepared by dissolving 36.2 g of $GaF_3 \cdot 3\ H_2O$ in 1000 ml distilled water. A 10.0 g sample of $NH_4$-ZSM-57 prepared in Example 15 is placed into a one-liter polypropylene bottle to which is then added 500 ml of the 0.2M $GaF_3$ This mixture is stirred and heated at 85° C. for 20 hours. After completion of the reaction, the product zeolite is filtered, washed with distilled water, dried, and found to be gallium-containing ZSM-57.

EXAMPLE 17

A 0.2M $FeF_3$ solution is prepared by dissolving 22.57 g $FeF_3$ in 1000 ml distilled water. A 500 ml quantity of the 0.2M $FeF_3$ solution is placed in a one-liter polypropylene bottle to which is then added 10.0 g of $NH_4$-ZSM-57 prepared in Example 15. This mixture is heated to 85° C. and stirred for 20 hours. After reaction, the product is filtered, washed with distilled water, dried under a heat lamp, and found to be iron-containing ZSM-57.

EXAMPLE 18

A 36.21 g quantity of $CrF_3 \cdot 4 H_2O$ crystals are dissolved in 1000 ml of distilled water to prepare 0.2M $CrF_3$ solution. A 500 ml quantity of the 0.2M $CrF_3$ solution is added to a one-liter polypropylene bottle. A 10.0 g sample of $NH_4$-ZSM-57 prepared in Example 15 is then added to the $CrF_3$ solution in the one-liter bottle and heated, with stirring, at 85° C. for 20 hours. After reaction, the product is filtered, washed with distilled water, dried in a hot air stream, and found to be chromium-containing ZSM-57.

What is claimed is:

1. A process for effecting catalytic conversion of an organic charge which comprises contacting said charge under catalytic conversion conditions with a catalyst comprising a catalytically effective amount of a synthetic porous crystalline zeolite having a molar ratio of $XO_2: Y_2O_3$ of at least 4, wherein X represents silicon and/or germanium and Y represents aluminum, boron, chromium, iron and/or gallium, said porous crystalline zeolite having at least the X-ray diffraction lines as set forth in Table 1 of the specification.

2. A process according to claim 1, wherein said zeolite is an aluminosilicate zeolite having a silica to alumina molar ratio of at least 4.

3. A process according to claim 1, wherein toluene is alkylated with methanol to produce xylenes, said process comprising contacting said toluene and said methanol with said catalyst under conditions comprising a temperature of from about 340° C. to about 500° C., a pressure of from about atmospheric to about 200 atmospheres, a weight hourly space velocity of from about 2 to about 2000 and a toluene to methanol mole ratio of from about 1:1 to about 20:1.

4. A process according to claim 3, wherein said zeolite is an aluminosilicate zeolite having a silica to alumina molar ratio of at least 4.

5. A process according to claim 1, wherein toluene is disproportionated to produce benzene and xylenes, said process comprising contacting said toluene with said catalyst under conditions comprising a temperature of from about 200° C. to about 760° C., a pressure of from about atmospheric to about 60 atmospheres and a weight hourly space velocity of from about 0.08 to about 20.

6. A process according to claim 5, wherein said zeolite is an aluminosilicate zeolite having a silica to alumina molar ratio of at least 4.

7. A process according to claim 1, wherein propane is converted to produce a mixture comprising light olefins and aromatics, said process comprising contacting said propane with said catalyst under conditions comprising a temperature of from about 100° C. to about 700° C., a pressure of from about 0.1 atmosphere to about 60 atmospheres, a weight hourly space velocity of from about 0.5 to about 400 and a hydrogen/propane mole ratio of from about 0 to about 20.

8. A process according to claim 7, wherein said zeolite is an aluminosilicate zeolite having a silica to alumina molar ratio of at least 4.

9. A process according to claim 1, wherein a refinery off gas is upgraded to produce liquid product enriched in BTX, said process comprising contacting said off gas with said catalyst under conditions comprising a temperature of from about 100° C. to about 700° C., a pressure of from about 0.1 atmosphere to about 60 atmospheres, a weight hourly space velocity of from about 0.5 to about 400 and a hydrogen to hydrocarbon mole ratio of from about 0 to about 20.

10. A process according to claim 1, wherein said charge comprises one or more $C_1$-$C_4$ alcohols and/or $C_2$-$C_4$ ethers and said alcohols and/or ethers are converted to hydrocarbons under conditions comprising a temperature of from about 300° C. to about 550° C., a pressure of from about 0.01 psi to about 2000 psi and a liquid hourly space velocity of from about 0.5 to about 100.

11. A process according to claim 10, wherein said conditions comprise a temperature of from about 370° C. to about 500° C., a pressure of from about 0.1 psi to about 500 psi, and a liquid hourly space velocity of from 0.5 to about 100.

12. A process according to claim 10, wherein said one or more alcohols and/or ethers is methanol.

* * * * *